United States Patent
Garg et al.

(10) Patent No.: US 12,087,122 B2
(45) Date of Patent: **\*Sep. 10, 2024**

(54) MOBILE SYSTEM FOR DISPENSING MEDICATION

(71) Applicant: CareFusion 303, Inc., San Diego, CA (US)

(72) Inventors: Honey Garg, San Diego, CA (US); Magnus R. Felke, San Diego, CA (US); Robert Gaede, San Diego, CA (US)

(73) Assignee: CareFusion 303, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/208,835

(22) Filed: Jun. 12, 2023

(65) Prior Publication Data

US 2023/0326283 A1 Oct. 12, 2023

Related U.S. Application Data

(63) Continuation of application No. 17/402,403, filed on Aug. 13, 2021, now Pat. No. 11,676,441, which is a
(Continued)

(51) Int. Cl.
*G07F 17/00* (2006.01)
*G16H 20/13* (2018.01)
(Continued)

(52) U.S. Cl.
CPC ......... *G07F 17/0092* (2013.01); *G16H 20/13* (2018.01); *H04W 4/80* (2018.02); *H04W 76/10* (2018.02)

(58) Field of Classification Search
CPC ..... G07F 17/0092; G16H 20/13; H04W 4/80; H04W 76/10
See application file for complete search history.

(56) References Cited

U.S. PATENT DOCUMENTS 10,299,992 B2 5/2019 Mullen
11,094,158 B2 * 8/2021 Garg .................. G07F 9/001
(Continued)

FOREIGN PATENT DOCUMENTS

CN 103699777 A 4/2014
CN 103838192 A 6/2014
(Continued)

OTHER PUBLICATIONS

Canadian Office Action for Application No. 3,106,705, dated Feb. 22, 2023, 5 pages.
(Continued)

*Primary Examiner* — Michael Collins
(74) *Attorney, Agent, or Firm* — Morgan, Lewis & Bockius LLP

(57) ABSTRACT

The subject technology provides at least a system and method for accessing a medication based on near-field communication (NFC). An NFC connection is established between a medical device and NFC circuitry associated with a user separate from the medical device and, based on information obtained from the NFC connection, pairing information for a mobile device to connect to the medical device is determined. A short range wireless connection is automatically established between the medical device and the mobile device associated with the user based on the determined pairing information, and a request for access to a medication provided by the medical device is sent from the mobile device to the medical device via the short range wireless connection.

20 Claims, 4 Drawing Sheets

Related U.S. Application Data continuation of application No. 16/530,911, filed on Aug. 2, 2019, now Pat. No. 11,094,158.

(60) Provisional application No. 62/716,302, filed on Aug. 8, 2018.

(51) Int. Cl.
*H04W 4/80* (2018.01)
*H04W 76/10* (2018.01)

(56) References Cited

U.S. PATENT DOCUMENTS

| | | | |
|---|---|---|---|
| 11,676,441 B2* | 6/2023 | Garg | H04W 4/80 700/236 |
| 2012/0003928 A1 | 1/2012 | Geboers | |
| 2012/0165975 A1* | 6/2012 | Yi | A61B 5/0022 235/462.1 |
| 2013/0262155 A1 | 10/2013 | Hinkamp | |
| 2013/0312066 A1 | 11/2013 | Suarez | |
| 2014/0277705 A1* | 9/2014 | Czaja | G16H 20/13 700/244 |
| 2014/0277707 A1 | 9/2014 | Akdogan | |
| 2015/0051730 A1 | 2/2015 | Portney | |
| 2015/0134358 A1 | 5/2015 | Fisher | |
| 2016/0188840 A1 | 6/2016 | Eramian et al. | |
| 2017/0095405 A1 | 4/2017 | Afsarifard | |
| 2017/0109498 A1 | 4/2017 | Childress | |
| 2017/0337157 A1 | 11/2017 | Rothschild | |
| 2018/0008516 A1 | 1/2018 | Afsarifard | |
| 2018/0028410 A1 | 2/2018 | Yun | |
| 2018/0248981 A1 | 8/2018 | Salem | |
| 2019/0205716 A1 | 7/2019 | Moshkovitz | |
| 2019/0392934 A1 | 12/2019 | Tabakin | |
| 2020/0236538 A1 | 7/2020 | Anslot | |
| 2020/0335193 A1 | 10/2020 | Zaker | |

FOREIGN PATENT DOCUMENTS

| | | |
|---|---|---|
| CN | 104662579 A | 5/2015 |
| WO | WO-2010044088 A1 | 4/2010 |
| WO | WO-2015131038 A2 | 9/2015 |

OTHER PUBLICATIONS

Chinese Office Action for Application No. 201980053818.0, dated Jun. 15, 2022, 12 pages including English translation.
Chinese Office Action for Application No. 201980053818.0, dated Oct. 27, 2021, 18 pages including English translation.
European Office Action for Application No. 19756072.5, dated Aug. 24, 2022, 9 pages.
International Search Report and Written Opinion for Application No. PCT/US2019/045336, dated Oct. 31, 2019, 13 pages.

* cited by examiner

MOBILE SYSTEM FOR DISPENSING MEDICATION

CROSS-REFERENCE TO RELATED APPLICATIONS

The present application is a continuation of U.S. patent application Ser. No. 17/402,403, filed on Aug. 13, 2021, now U.S. Pat. No. 11,676,441, which is a continuation application of U.S. patent application Ser. No. 16/530,911, filed Aug. 2, 2019, now U.S. Pat. No. 11,094,158, which claims the benefit of U.S. Provisional Patent Application Ser. No. 62/716,302, filed Aug. 8, 2018, the entirety of each of which is incorporated herein by reference for all purposes.

In one or more implementations, not all of the depicted components in each figure may be required, and one or more implementations may include additional components not shown in a figure. Variations in the arrangement and type of the components may be made without departing from the scope of the subject disclosure. Additional components, different components, or fewer components may be utilized within the scope of the subject disclosure.

DETAILED DESCRIPTION

The detailed description set forth below is intended as a description of various implementations and is not intended to represent the only implementations in which the subject technology may be practiced. As those skilled in the art would realize, the described implementations may be modified in various different ways, all without departing from the scope of the present disclosure. Accordingly, the drawings and description are to be regarded as illustrative in nature and not restrictive.

Automated medication dispensing systems can be used to support decentralized medication management with various features to enhance safety and efficiency. By way of example, such systems may help clinicians accurately dispense medications and may support pharmacy workflows through use of secure authentication and automated tracking of medication inventory and access.

One example of an automated medication dispensing system can employ a computer coupled locally to a medication dispensing device, such as a refrigerator or dispensing cabinet providing a locked container for storing a medication. The local computer can provide a user interface for nurses or other practitioners to access the medication locked in the dispensing device, as well as provide functionality for communicating with a remote server to receive medication orders from the server or provide dispense information to the server to update a database. However, space constraints may make the implementation of a local computer in an automated medication dispensing system impractical, and moreover, the use of a local computer can lead to inefficient queues in cases where multiple nurses need to access the same medication dispensing device to treat multiple patients in a common facility.

Figure 1:
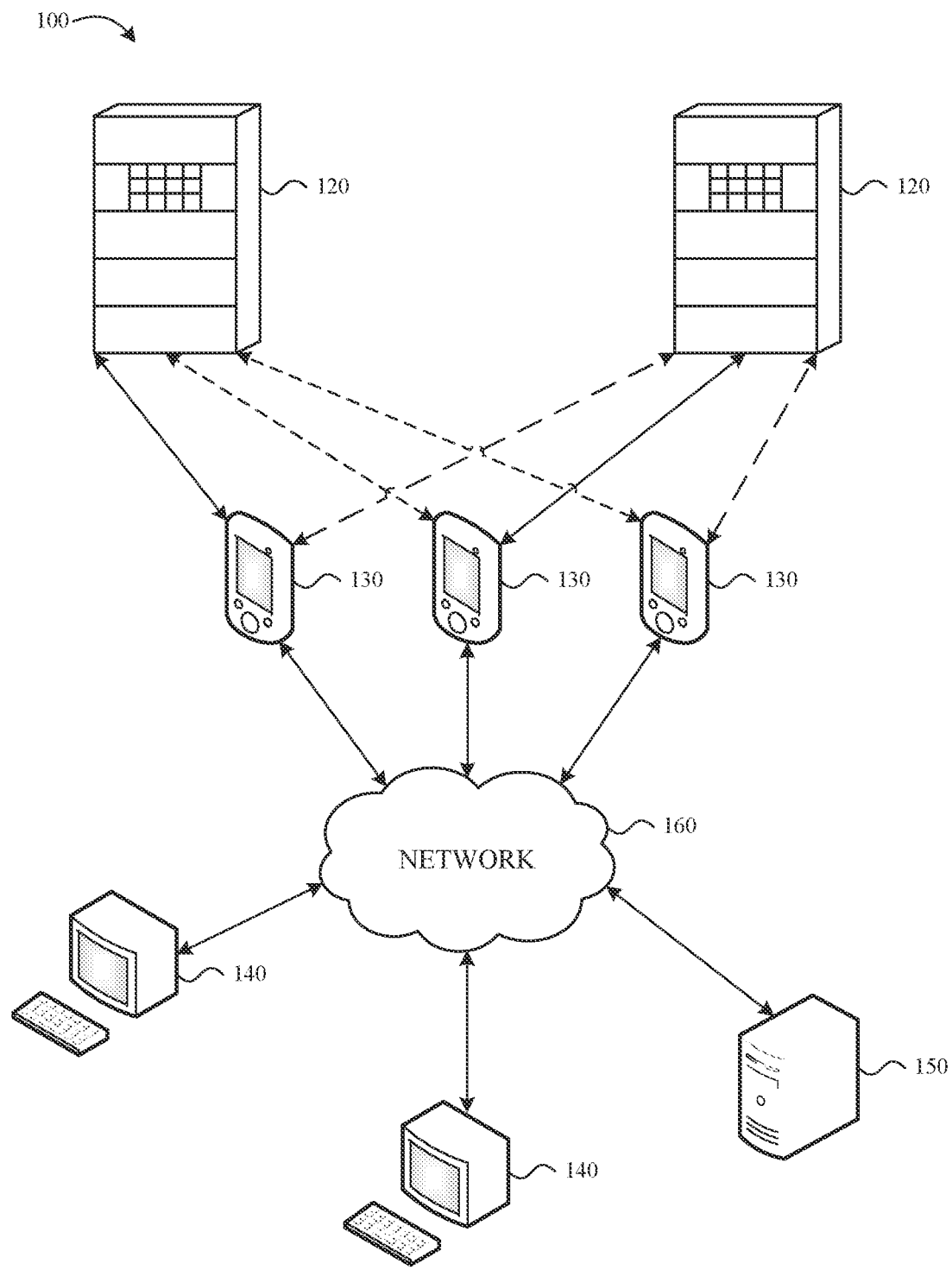
FIG. 1 is a schematic diagram of an example of a medication management system.

FIG. 1 is a schematic diagram illustrating an example medication management system 100. The medication management system 100 includes or otherwise involves medication dispensing devices 120, mobile devices 130, electronic medical record (EMR) terminals 140, a server 150, and a network 160. Each of the medication dispensing devices 120 can include a container configured to hold medication, which can be unlocked or otherwise accessed via local or short range communication with mobile devices 130. Each of the mobile devices 130 can be configured to communicate with a remote server 150 over network 160 to receive medication order information and/or to send dispense information to the server 150 to allow the server 150 to update data.

Each of the mobile devices 130 can, for example, be implemented as a smart phone, tablet computer, a wearable device (e.g., a smart watch), or any other appropriate portable communication device capable of running an application (e.g., a mobile app) and communicating with the medication dispensing devices 120 via Bluetooth®, near-field communication (NFC), Wi-Fi, or other appropriate short range wireless interface. In FIG. 1, a plurality of mobile devices 130 and a plurality of medication dispensing devices 120 are included in which each mobile device 130 is configured to communicate with multiple medication dispensing devices 120, and likewise each medication dispensing device 120 is configured to communicate with multiple medical devices 130. This may allow for a flexible framework in which computing devices associated with receiving medication orders and/or unlocking the medication dispensing devices 120 can travel with a nurse or other practitioner, rather than being tied to individual medication dispensing devices 120. This can also, for example, allow a nurse or other practitioner to queue medication orders in the mobile device 130, without having to queue up at a local terminal to enter the orders. However, while multiple medication dispensing devices 120 and multiple mobile devices 130 are included in the example medication management system 100 and can be configured to communicate as described above, other implementations are possible. For example, in some implementations only one mobile device 130 or any other suitable number of mobile devices can be included. Additionally or alternatively, only one medication dispensing device 120 or any other suitable number of dispensing devices can be included. Additionally or alternatively, each mobile device 130 can be configured to communicate with only one or any other suitable subset of medication dispensing devices 120. Additionally or alternatively, each medication dispensing device 120 can be configured to communicate with only one or any other suitable subset of the mobile devices 130.

When a particular mobile device 130 and medication dispensing device 120 are in sufficiently close proximity to one another, communication between the mobile device 130 and the medication dispensing device 120 may be established through the short range wireless interface so that the mobile device 130 can provide commands to the medication dispensing device 120 to unlock or access medication stored therein. Additionally or alternatively, the communication can allow the mobile device 130 to obtain medication dispensing or inventory information from the medication dispensing device 120. The use of short range or local communication between the mobile device 130 and medication dispensing device 120 may enhance security and safety by constraining the mobile devices 130 to only be capable of unlocking or accessing the medication dispensing device 120 when in sufficiently close proximity to each other.

In some implementations, the subject technology enables automatic pairing (e.g., when the short range wireless interface is a Bluetooth interface) of a particular mobile device 130 to a particular medication dispensing device 120, facilitated by an NFC link established by NFC circuitry provided by the particular mobile device 130, or a badge associated with a clinician. According to various implementations, both the mobile device 130 and the medication dispensing device 120 may include NFC circuitry such that when within range of each other a connection (e.g., an NFC link) is triggered between the two devices. For example, communication between the two NFC supported devices can occur when the particular mobile device 130 is brought in close proximity (e.g., within NFC range corresponding to no more than 91 centimeters) with the particular medication dispensing device 120, which activates the respective NFC circuitry on each device allowing for an automated establishment the NFC link. This link is used to quickly provide pairing information so that a secondary wireless connection between the devices may be automatically established using a peer-to-peer pairing process without the need to prompt the clinician to manually select (e.g., from a list) the medication dispensing device, or the need for access credentials to complete the pairing process. The link may be used to transmit other parameters related to the particular medication dispensing device 120. Such other parameters may include, for example, hash information, randomized information, Bluetooth local name, service class identifier, class of device information, etc., that can be utilized as part of an authentication process.

The particular medication dispensing device 120 may include active or passive NFC circuitry to enable NFC-related communication between the two devices, and to transmit the pairing information and/or related parameters. When the mobile device 130 includes active NFC circuitry, the mobile device may directly receive the pairing information and/or parameters from the medication dispensing device 120. In some implementations, the clinician's badge may be used to initiate the NFC communication. Passive NFC circuitry in the badge may transmit to the medication dispensing device an identifier of the clinician. The medication dispensing device may then send the pairing information (including any related parameters) to a centralized server 150 with the identifier, and the server may push the information to the mobile device. In this regard, the mobile device 130 receives the information and may automatically initiate and complete the secondary wireless connection using the received information. The server may also perform a check on the clinician's authorization to access the medication dispensing device before providing the information to the mobile device, and/or may provide authentication information to the mobile device which may then be passed over the secondary wireless connection to the medication dispensing device for authentication at the medication dispensing device.

The secondary wireless connection may be a Bluetooth connection. Each of the medication dispensing devices 120 may include a Bluetooth low energy (BLE) beacon, or other appropriate wireless transmitter or transceiver, beacon, or interface capable of communicating with the mobile device (s) 130. When the NFC connection is established, the medication dispensing device 120 may send over the NFC connection, to the mobile device 130, an address (e.g., a MAC address) of the BLE beacon associated with the medication dispensing device 120. The mobile device 130 may then use this address to automatically connect to the BLE beacon of the medication dispensing device 120, automatically, and to begin communications. In some implementations, a pairing PIN code may also be sent over the NFC connection so that the pairing may be securely established between the two devices, without the need to prompt the clinician to manually confirm the PIN code when the pairing process is initiated. After completing the authentication process, the particular mobile device 130 and the particular medication dispensing device 120 may then be automatically paired, via Bluetooth, based at least in part on the device address of the particular medication dispensing device 120 and the other parameters related to the particular medication dispensing device 120.

The foregoing solution speeds up the pairing and connection process by establishing a fast connection between two devices. The NFC link facilitates a pairing process (e.g., via Bluetooth) between the two devices that provides a different communication link (e.g., a Bluetooth connection) which advantageously provides higher network bandwidth, throughput and/or range capabilities to support more sophisticated functionality than the NFC link.

In some implementations, multiple medication dispensing devices 120 may be linked, and each dispensing device may be configured to, receive a request or order for a medication, and locate the medication in another linked device. In this regard, the particular mobile device 120 of clinician may automatically connect to one medication dispensing device 120 to enter an order for one or more medications, irrespective of where those medications may be stored, and without the need to queue up with other clinicians at a single terminal. In some implementations, the pairing process at a particular medication dispensing device 120 may prevent, or lock out, other clinicians from pairing to or accessing medication in the device while the particular mobile device 130 of the clinician is paired to the particular medication dispensing device 120. In some implementations, the particular medication dispensing device 120 may be configured for multiple pairings, but may restrict access to medication in a single device based on a software queue.

For example, multiple clinicians may connect to a first medication dispensing device 120 using the previously-described wireless pairing process, and enter orders simultaneously for various medications. A first and second requested medication may be available at the first medication dispensing device, while a third requested medication is available at a second medication dispensing device. The system may require a second clinician who placed an order for the second requested medication to wait for a first clinician who placed an order for the first requested medication to retrieve the first requested medication before the second clinician is provided access to the first medication dispensing device. However, a third clinician may be able to place an order for the third medication and the second medication dispensing device while the others access the first medication dispensing device.

Each mobile device 130 can, for example, employ secure authentication such as biometric authentication, passcode authentication, and/or other credentials to avoid unauthorized access, for example, by somebody other than an authorized nurse or other practitioner in possession of the mobile device 130. Some examples of biometric authentication include fingerprint authentication, facial recognition, and iris authentication. Some examples of passcode authentication include pincodes, passwords, and other knowledge based authentication factors. As described previously, this information may be passed by the NFC link, or over the Bluetooth connection during the pairing process to authenticate the clinician to the respective medication dispensing device 120.

Each medication dispensing device 120 may, for example, be implemented as a refrigerator, automated dispensing cabinet, or a combination thereof, which contains one or more containers configured to store a medication therein. The dispensing device(s) 120 may also, for example, include a locking mechanism or other appropriate access control mechanism for allowing access to the container or dispensing of the medication only when appropriate commands are received from the mobile devices 130 via the BLE beacon or other local communication interface.

The mobile device(s) 130 can each also include a network interface for communicating with a remote server 150 over a network 160, such as the internet or another appropriate data network. The mobile device(s) 130 can include an application or other appropriate programming that configures the mobile device(s) 130 to receive medication order information from the server 150 associated with medications to be accessed from the dispensing devices 120. Additionally or alternatively, the mobile device(s) 130 can be configured to provide commands to the medication dispensing device(s) 120 to unlock a container to access a medication stored therein. Additionally or alternatively, the mobile device(s) 130 can be configured to provide medication dispensing information to the server 150, in which the medication dispensing information is associated with medication dispensing event(s) involving the medication dispensing device 120.

The mobile device(s) 130 can, for example, include one or more input devices and/or output devices, which can provide a user interface for receiving inputs from a user and/or providing outputs to a user associated with medication. For example, the user interface can output a notification upon receipt of a new medication order from the server 150 (e.g., a push notification), and/or the user interface provide for input to select particular patients or medication, or to initiate unlocking or access of a container in the medication dispensing device 120. Examples of input devices include touchscreens, touchpads, microphones, buttons, and any other devices that allow for interaction from a user to input information or provide commands through the mobile device. Examples of output devices include display, speakers, haptic vibrations, and other appropriate devices that allow for interaction with a user to communicate information to the user. Examples of user interfaces that can be provided in the mobile devices 130 are shown in FIGS. 3A-3D below.

The server 150 may, for example, be implemented as a physical and/or cloud based server operated on one or several computing devices that can coordinate with the mobile devices 130 to provide medication order information and/or receive medication dispensing information. Additionally or alternatively, the server 150 can coordinate with EMR terminals 140 other appropriate devices to receive medication orders from a doctor or other medical practitioner capable of prescribing medications. The server 150 can be configured to receive a medication order input into a patient's EMR or other electronic record through the EMR terminal(s) 140, and coordinate with an application running on the mobile devices 130 to provide the medication order information to the appropriate nurses or practitioners. Additionally or alternatively, the server 150 can be configured to update or maintain a pharmacy information system (PIS) or other medication related data based on dispense information received from the mobile devices 130.

Figure 2:
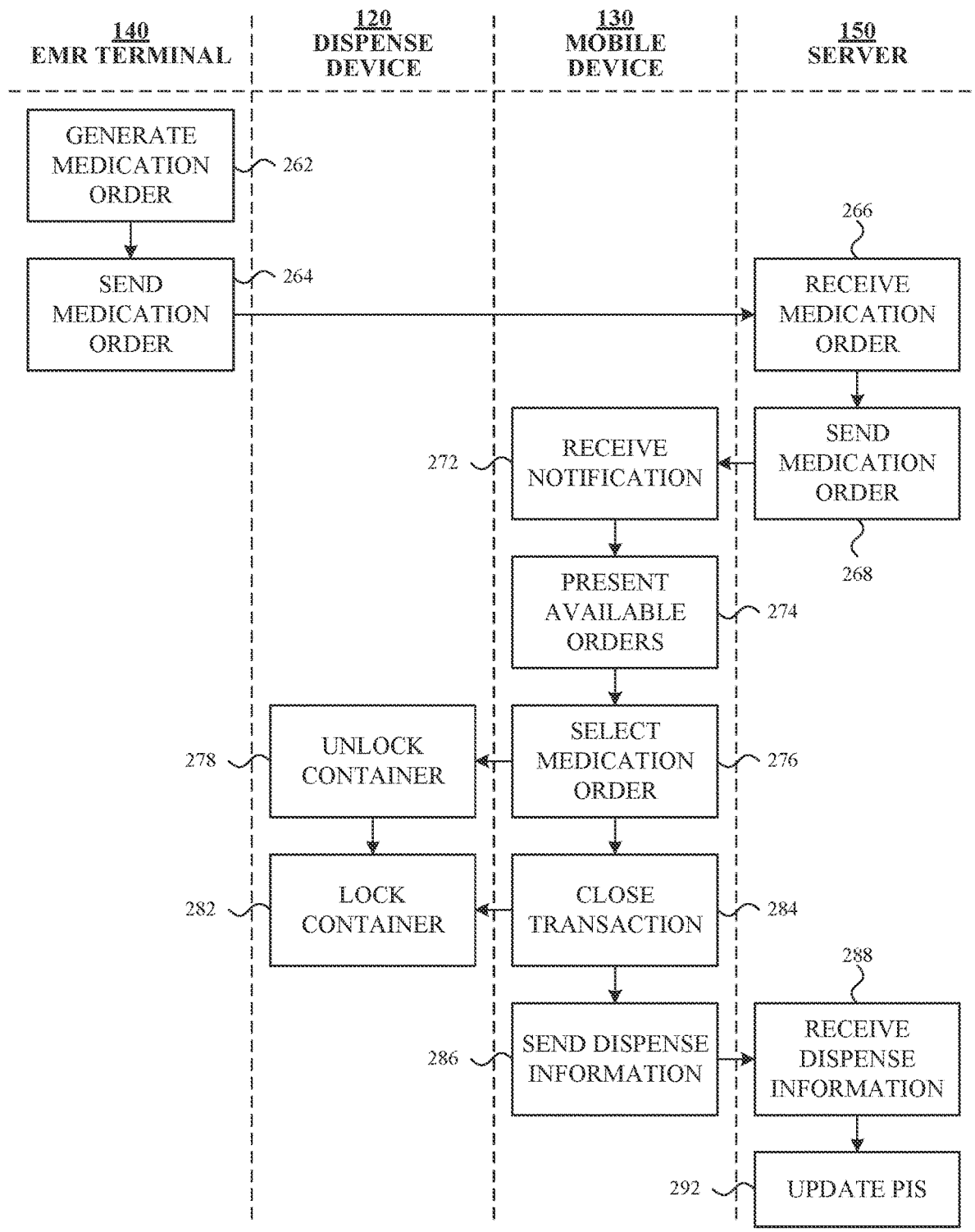
FIG. 2 is a flow diagram of an example method of managing medication.

FIG. 2 is flow diagram illustrating an example method 200 for medication management. The method 200 may, for example, be implemented using the medication management system 100 shown in FIG. 1. FIGS. 3A-3D are examples of user interfaces 300a-300d that may, for example, be implemented in a mobile device in connection with the method 200.

As shown in FIG. 2, at 262, a new medication order can be generated at an EMR terminal 140 based on a doctor or other appropriate medical professional (e.g., an MD) ordering medication for a patient in an EMR or other appropriate electronic record. The medication order can include information identifying a medication (or drug) to be provided to a particular patient. At 264, the EMR terminal 140 sends the medication order otherwise sends information regarding the medication order to server 150 over a network (e.g., network 160).

At 266, the server 150 receives the medication order or otherwise receives information regarding medication order. At 268, the server 150 sends the medication order or otherwise sends information regarding the medication order to a mobile device 130 over a network, e.g., through a mobile application running on the mobile device.

At 272, the mobile device receives a notification of the new medical order from the server 150. At this stage, the mobile device 130, can, for example, present a notification (e.g., a push notification) of the new medication order through a user interface, such as is shown in the example display interface 300a shown in FIG. 3A. Alternatively, the notification need not be presented, and the user can simply see the medication order information when the user chooses to open or otherwise access the application on the mobile device 130.

Figure 3A:
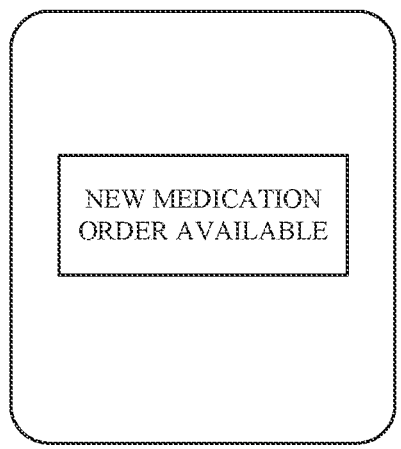
FIGS. 3A-3D are examples of user interfaces that may be employed in a medication management system.
Figure 3B:
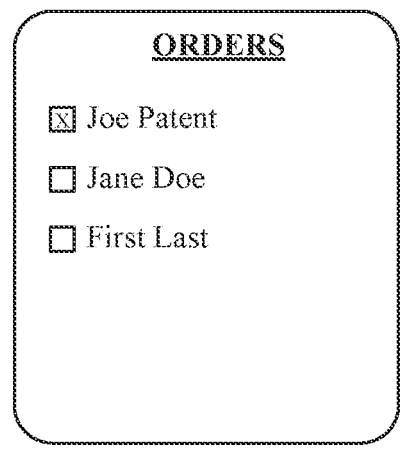
Figure 3C:
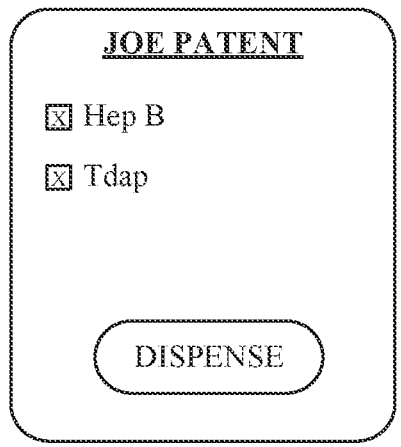

At 274, upon a user (e.g., a nurse or practitioner) accessing the application, the mobile device 130 can present all available medication orders, or patients having outstanding medication orders, or otherwise present information regarding the same through an appropriate user interface. An example of a display interface 300b showing a listing of several patients having corresponding medication orders is shown in FIG. 3B. The user interface can also provide for the user to select the desired patient and/or medication for a patient, e.g., through user input to an appropriate input device. Examples of display interfaces 300b and 300c showing selection of a patient, and medications for a particular patient, are shown in FIGS. 3B and 3C respectively.

At 276, the mobile device 130 selects a medication corresponding to the medication order based on received user input. For example, the medication may be selected upon the user selecting the appropriate patients and their appropriate medication(s), and selecting "dispense" as shown in the display interface 300c in FIG. 3C. Upon selection of the medication, the mobile device 130 can automatically connect, as described above, to a medication dispensing device 120 within sufficiently close proximity to the mobile device 130, and communicate the selection to the medication dispensing device 120 or otherwise communicate an indication of the medication order, and send a command or otherwise initiate dispensing of the medication from the medication dispensing device 120. Although not shown in FIG. 2, as described above, the mobile device 130 can establish a connection to an appropriate medication dispensing device 120, e.g., via a Bluetooth pairing, before or after the medication order is received or selected. If the connected medication dispensing device does not currently store the requested medication corresponding to the medication order then the connected medication dispensing device may inform the mobile device (and the clinician) of the location of another medication dispensing device where the medication can be retrieved.

At 278, the medication dispensing device 120 (identified as containing the medication) unlocks an appropriate container containing the medication corresponding to the medication order, or otherwise dispenses the medication housed within the medication dispensing device 120. The medication dispensing device 120 may be configured to only unlock the container or otherwise dispense the medication when the mobile device 130 is identified as being within a range of or paired with the medication dispensing device 120 (e.g., as described above), and the clinician appropriately authenticated to the device. The dispense device 120 can be configured to unlock the container or otherwise dispense the medication upon receipt of a command or other appropriate communication from the mobile device 130 over the short range wireless interface. If the medication dispensing device 120 contains multiple containers or compartments corresponding to multiple medications, the medication dispensing device 120 can, for example, be configured to unlock only the container or containers containing the selected medication or medications corresponding to the medication order.

Figure 3D:
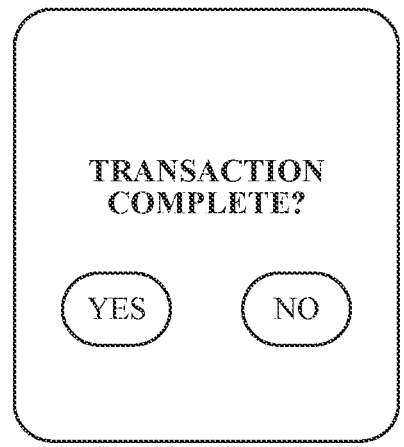

At 284, the mobile device 130 can close the medication dispensing transaction, for example, based on confirmation or other user input from the user. An example of a display interface 300*d* providing for a user to close the transaction after the desired medication is retrieved is shown in FIG. 3D.

At 282, after unlocking the container the medication dispensing device 120 locks the container from which the medication was dispensed and retrieved by the user. The container can, for example, lock upon the mobile device 130 closing the transaction and sending a command or other communication to the medication dispensing device 120 indicating that the dispense transaction has been completed. Additionally or alternatively, the container can lock again automatically, e.g., after a fixed period of time for security.

At 286, the mobile device 130 sends dispense information to the server 150 over the network. The dispense information can, for example, be sent upon closing the transaction (e.g., upon a nurse selecting "yes" in the display interface 300*d* shown in FIG. 3D). The dispense information can, for example, include an amount and/or type of medication dispensed, a time of the dispense event, or other information associated with the medication dispense event. The dispense information can, for example, be based on monitoring performed automatically by the medication dispensing device 120.

At 288, the server 150 receives the dispense information from the mobile device 130. At 292, the server 150 updates a pharmacy information system (PIS) included in or otherwise coupled to the server 150, based on the dispense information associated with the dispense event.

Figure 4:
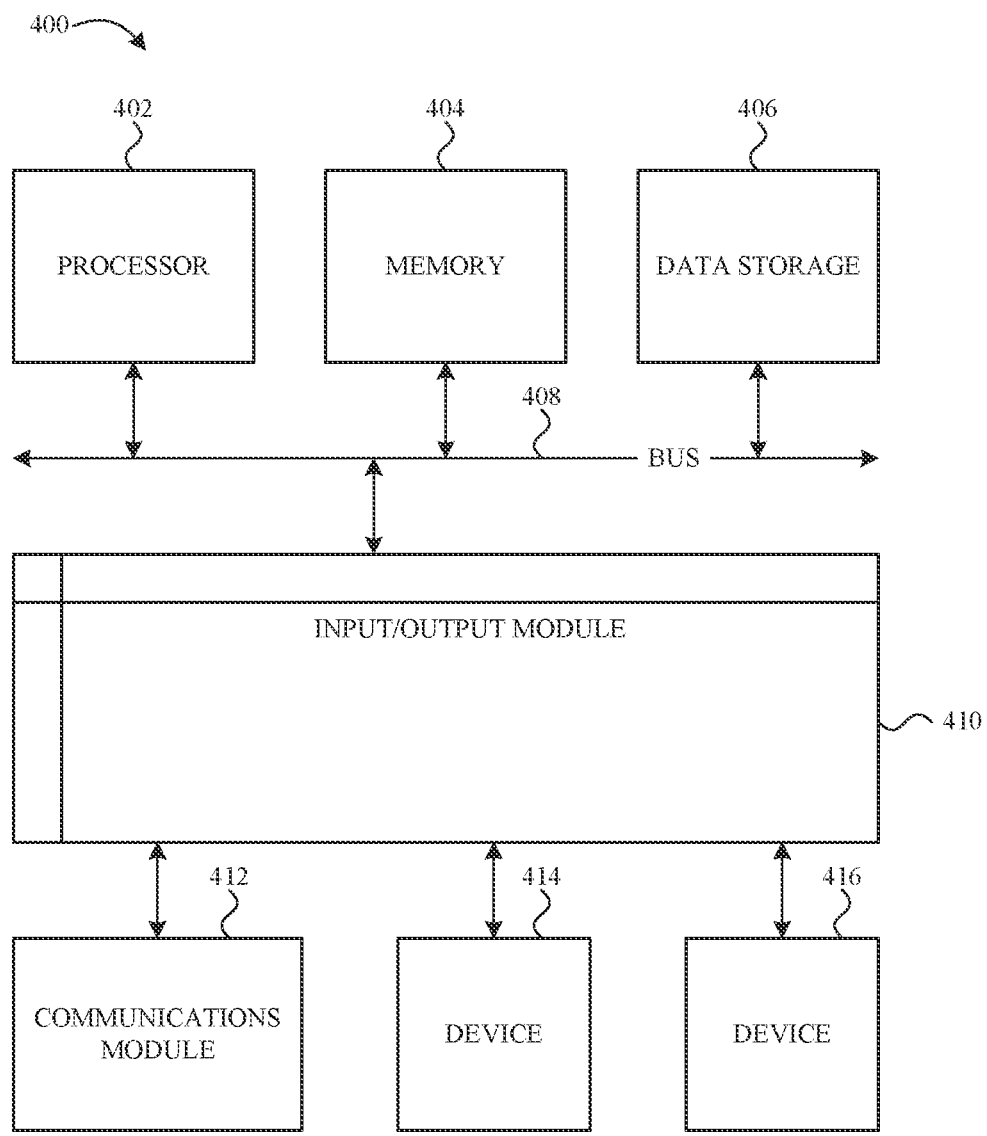
FIG. 4 is a block diagram of an example of a computer system that may be implemented in a medication management system.

FIG. 4 is a block diagram illustrating an example computer system 400 with which any one or more of the mobile device(s) 130, the EMR terminal(s) 140, or the server(s) 150 may be implemented.

Computer system 400 includes a bus 408 or other communication mechanism for communicating information, and a processor 402 coupled with bus 408 for processing information. By way of example, the computer system 400 may be implemented with one or more processors 402. Processor 402 may be a general-purpose microprocessor, a micro control module, a Digital Signal Processor (DSP), an Application Specific Integrated Circuit (ASIC), a Field Programmable Gate Array (FPGA), a Programmable Logic Device (PLD), a control module, a state machine, gated logic, discrete hardware components, or any other suitable entity that can perform calculations or other manipulations of information.

Computer system 400 can include, in addition to hardware, a code that creates an execution environment for the computer program in question, e.g., code that constitutes processor firmware, a protocol stack, a database management system, an operating system, or a combination of one or more of them stored in an included memory 404, such as a Random Access Memory (RAM), a flash memory, a Read Only Memory (ROM), a Programmable Read-Only Memory (PROM), an Erasable PROM (EPROM), registers, a hard disk, a removable disk, a CD-ROM, a DVD, or any other suitable storage device, coupled to bus 408 for storing information and instructions to be executed by processor 402. The processor 402 and the memory 404 can be supplemented by, or incorporated in, a special purpose logic circuitry.

The instructions may be stored in the memory 404 and implemented in one or more computer program products, i.e., one or more modules of computer program instructions encoded on a computer readable medium for execution by, or to control the operation of, the computer system 400, and according to any method well known to those skilled in the art, including, but not limited to, computer languages such as data-oriented languages (e.g., SQL, dBase), system languages (e.g., C, Objective-C, C++, Assembly), architectural languages (e.g., Java, .NET), and application languages (e.g., PHP, Ruby, Perl, Python). Instructions may also be implemented in computer languages such as array languages, aspect-oriented languages, assembly languages, authoring languages, command line interface languages, compiled languages, concurrent languages, curly-bracket languages, dataflow languages, data-structured languages, declarative languages, esoteric languages, extension languages, fourth-generation languages, functional languages, interactive mode languages, interpreted languages, iterative languages, list-based languages, little languages, logic-based languages, machine languages, macro languages, metaprogramming languages, multiparadigm languages, numerical analysis, non-English-based languages, object-oriented class-based languages, object-oriented prototype-based languages, off-side rule languages, procedural languages, reflective languages, rule-based languages, scripting languages, stack-based languages, synchronous languages, syntax handling languages, visual languages, wirth languages, and xml-based languages. Memory 404 may also be used for storing temporary variable or other intermediate information during execution of instructions to be executed by processor 402.

A computer program as discussed herein does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, subprograms, or portions of code). A computer program can be deployed to be executed on one computer or on multiple computers that are located at one site or distributed across multiple sites and interconnected by a communication network. The processes and logic flows described in this specification can be performed by one or more programmable processors executing one or more computer programs to perform functions by operating on input data and generating output.

Computer system 400 further includes a data storage device 406, such as a magnetic disk or optical disk, coupled to bus 408 for storing information and instructions. Computer system 400 may be coupled via input/output module 410 to various devices. Input/output module 410 can be any input/output module. Exemplary input/output modules 410 include data ports such as USB ports. Input/output module 410 is configured to connect to a communications module 412. Exemplary communications modules 412 include networking interface cards, such as Ethernet cards and modems. In certain aspects, input/output module 410 is configured to connect to a plurality of devices, such as an input device 414 and/or an output device 416. Examples of input devices 414 include a keyboard and a pointing device, e.g., a mouse or a trackball, by which a user can provide input to the computer system 400. Other kinds of input devices 414 can be used to provide for interaction with a user as well, such as a tactile input device, visual input device, audio input device, or brain-computer interface device. For example, feedback provided to the user can be any form of sensory feedback, e.g., visual feedback, auditory feedback, or tactile feedback; and input from the user can be received in any form, including acoustic, speech, tactile, or brain wave input. Examples of output devices 416 include display devices, such as an LCD (liquid crystal display) monitor, for displaying information to the user.

According to one aspect of the present disclosure, method 200 or any portion thereof can be implemented using a computer system 400 in response to processor 402 executing one or more sequences of one or more instructions contained in memory 404. Such instructions may be read into memory 404 from another machine-readable medium, such as data storage device 406. Execution of the sequences of instructions contained in main memory 404 causes processor 402 to perform the process steps described herein. One or more processors in a multi-processing arrangement may also be employed to execute the sequences of instructions contained in memory 404. In alternative aspects, hard-wired circuitry may be used in place of or in combination with software instructions to implement various aspects of the present disclosure. Thus, aspects of the present disclosure are not limited to any specific combination of hardware circuitry and software.

Various aspects of the subject matter described in this specification can be implemented in a computing system that includes a back-end component, e.g., as a data server, or that includes a middleware component, e.g., an application server, or that includes a front-end component, e.g., a client computer having a graphical user interface or a Web browser through which a user can interact with an implementation of the subject matter described in this specification, or any combination of one or more such back-end, middleware, or front-end components. The components of the system can be interconnected by any form or medium of digital data communication, e.g., a communication network. The communication network (e.g., network 160) can include, for example, any one or more of a LAN, a WAN, the Internet, and the like. Further, the communication network can include, but is not limited to, for example, any one or more of the following network topologies, including a bus network, a star network, a ring network, a mesh network, a star-bus network, tree or hierarchical network, or the like. The communications modules can be, for example, modems or Ethernet cards.

Computer system 400 can include clients and servers. Any one or more of the mobile devices 130 and/or EMR terminals 140 can, for example, be configured as a client to the server 150. A client and server are generally remote from each other and typically interact through a communication network. The relationship of client and server arises by virtue of computer programs running on the respective computers and having a client-server relationship with each other. Computer system 400 can be, for example, and without limitation, a desktop computer, laptop computer, or tablet computer. Computer system 400 can also be embedded in another device, for example, and without limitation, a mobile telephone, a PDA, a mobile audio player, a Global Positioning System (GPS) receiver, a video game console, and/or a television set top box.

The term "machine-readable storage medium" or "computer readable medium" as used herein refers to any medium or media that participates in providing instructions to processor 402 for execution. Such a medium may take many forms, including, but not limited to, non-volatile media, volatile media, and transmission media. Non-volatile media include, for example, optical or magnetic disks, such as data storage device 406. Volatile media include dynamic memory, such as memory 404. Transmission media include coaxial cables, copper wire, and fiber optics, including the wires that include bus 408. Common forms of machine-readable media include, for example, floppy disk, flexible disk, hard disk, magnetic tape, any other magnetic medium, CD-ROM, DVD, any other optical medium, punch cards, paper tape, any other physical medium with patterns of holes, a RAM, a PROM, an EPROM, a FLASH EPROM, any other memory chip or cartridge, or any other medium from which a computer can read. The machine-readable storage medium can be a machine-readable storage device, a machine-readable storage substrate, a memory device, a composition of matter affecting a machine-readable propagated signal, or a combination of one or more of them. The computer readable medium can be non-transitory.

A reference to an element in the singular is not intended to mean one and only one unless specifically so stated, but rather one or more. For example, "a" module may refer to one or more modules. An element proceeded by "a," "an," "the," or "said" does not, without further constraints, preclude the existence of additional same elements.

Headings and subheadings, if any, are used for convenience only and do not limit the invention. The word exemplary is used to mean serving as an example or illustration. To the extent that the term include, have, or the like is used, such term is intended to be inclusive in a manner similar to the term comprise as comprise is interpreted when employed as a transitional word in a claim. Relational terms such as first and second and the like may be used to distinguish one entity or action from another without necessarily requiring or implying any actual such relationship or order between such entities or actions.

Phrases such as an aspect, the aspect, another aspect, some aspects, one or more aspects, an implementation, the implementation, another implementation, some implementations, one or more implementations, an embodiment, the embodiment, another embodiment, some embodiments, one or more embodiments, a configuration, the configuration, another configuration, some configurations, one or more configurations, the subject technology, the disclosure, the present disclosure, other variations thereof and alike are for convenience and do not imply that a disclosure relating to such phrase(s) is essential to the subject technology or that such disclosure applies to all configurations of the subject technology. A disclosure relating to such phrase(s) may apply to all configurations, or one or more configurations. A disclosure relating to such phrase(s) may provide one or more examples. A phrase such as an aspect or some aspects may refer to one or more aspects and vice versa, and this applies similarly to other foregoing phrases.

A phrase "at least one of" preceding a series of items, with the terms "and" or "or" to separate any of the items, modifies the list as a whole, rather than each member of the list. The phrase "at least one of" does not require selection of at least one item; rather, the phrase allows a meaning that includes at least one of any one of the items, and/or at least one of any combination of the items, and/or at least one of each of the items. By way of example, each of the phrases "at least one of A, B, and C" or "at least one of A, B, or C" refers to only A, only B, or only C; any combination of A, B, and C; and/or at least one of each of A, B, and C.

It is understood that the specific order or hierarchy of steps, operations, or processes disclosed is an illustration of exemplary approaches. Unless explicitly stated otherwise, it is understood that the specific order or hierarchy of steps, operations, or processes may be performed in different order. Some of the steps, operations, or processes may be performed simultaneously. The accompanying method claims, if any, present elements of the various steps, operations or processes in a sample order, and are not meant to be limited to the specific order or hierarchy presented. These may be performed in serial, linearly, in parallel or in different order. It should be understood that the described instructions, operations, and systems can generally be integrated together in a single software/hardware product or packaged into multiple software/hardware products.

The disclosure is provided to enable any person skilled in the art to practice the various aspects described herein. In some instances, well-known structures and components are shown in block diagram form in order to avoid obscuring the concepts of the subject technology. The disclosure provides various examples of the subject technology, and the subject technology is not limited to these examples. Various modifications to these aspects will be readily apparent to those skilled in the art, and the principles described herein may be applied to other aspects.

All structural and functional equivalents to the elements of the various aspects described throughout the disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112(f) or § 112, sixth paragraph, unless the element is expressly recited using the phrase "means for" or, in the case of a method claim, the element is recited using the phrase "step for".

The title, background, brief description of the drawings, abstract, and drawings are hereby incorporated into the disclosure and are provided as illustrative examples of the disclosure, not as restrictive descriptions. It is submitted with the understanding that they will not be used to limit the scope or meaning of the claims. In addition, in the detailed description, it can be seen that the description provides illustrative examples and the various features are grouped together in various implementations for the purpose of streamlining the disclosure. The method of disclosure is not to be interpreted as reflecting an intention that the claimed subject matter requires more features than are expressly recited in each claim. Rather, as the claims reflect, inventive subject matter lies in less than all features of a single disclosed configuration or operation. The claims are hereby incorporated into the detailed description, with each claim standing on its own as a separately claimed subject matter.

The claims are not intended to be limited to the aspects described herein, but are to be accorded the full scope consistent with the language of the claims and to encompass all legal equivalents. Notwithstanding, none of the claims are intended to embrace subject matter that fails to satisfy the requirements of the applicable patent law, nor should they be interpreted in such a way.

What is claimed is:

1. A method of accessing a medication, the method comprising:
    establishing a first short range wireless connection between a medication dispensing cabinet and a first mobile device circuitry associated with a user;
    determining, based on information obtained from the first short range wireless connection, pairing information for a second mobile device circuitry to connect to the medication dispensing cabinet using a different type of connection;
    automatically establishing a second short range wireless connection, different than the first short range wireless connection, between the medication dispensing cabinet and the second mobile device circuitry based on the pairing information; and
    receiving, from the second mobile device circuitry at the medication dispensing cabinet via the second short range wireless connection, a request for access to the medication dispensing cabinet; and
    causing to be provided, based on the request, access to a medication within the medication dispensing cabinet.

2. The method of claim 1, wherein the medication dispensing cabinet comprises a plurality of lockable containers, the method further comprising:
    authorizing the user to dispense the medication for a patient; and
    unlocking only a container of the plurality of locking containers that stores the medication based on the request for access and the authorizing.

3. The method of claim 2, further comprising:
    receiving an indication that the medication was dispensed from the container; and
    automatically locking the container responsive to receiving the indication.

4. The method of claim 2, further comprising:
    receiving, at the medication dispensing cabinet, from the first mobile device circuitry via the first short range wireless connection, biometric authentication information,
    wherein the authorizing is based on the biometric authentication information.

5. The medication dispensing cabinet of claim 2, further comprising:
    receive an indication that the medication was dispensed from the container; and
    automatically lock the container responsive to receiving the indication.

6. The medication dispensing cabinet of claim 2, further comprising:
    receive, at the medication dispensing cabinet, from the first mobile device circuitry via the first short range wireless connection, biometric authentication information,
    wherein the authorizing is based on the biometric authentication information.

7. The medication dispensing cabinet of claim 6, wherein the obtained information comprises a user identification for the user, the method further comprising:
receive the user identification via the first short range wireless connection; and
authorize the user based on the user identification,
wherein the pairing information is determine in response to authorizing the user based on the user identification.

8. The medication dispensing cabinet of claim 7, wherein authorizing the user based on the user identification comprises:
provide the user identification and the pairing information to a server,
wherein the server provides the pairing information to the second mobile device circuitry.

9. The method of claim 1, wherein the obtained information comprises a user identification for the user, the method further comprising:
receiving the user identification via the first short range wireless connection; and
authorizing the user based on the user identification,
wherein the pairing information is determine in response to authorizing the user based on the user identification.

10. The method of claim 9, wherein authorizing the user based on the user identification comprises:
providing the user identification and the pairing information to a server,
wherein the server provides the pairing information to the second mobile device circuitry.

11. The method of claim 1, further comprising:
providing the pairing information to the first mobile device circuitry via the first short range wireless connection;
receiving, after providing the pairing information, a connection request from the second mobile device circuitry to establish the second short range wireless connection; and
establishing the second short range wireless connection responsive to the connection request,
wherein the first mobile device circuitry and second mobile device circuitry are different communication circuitries implemented on a user device.

12. A method of accessing a medication, the method comprising:
establishing a first short range wireless connection between a medication dispensing cabinet and a mobile device associated with a user;
determining, based on information obtained from the first short range wireless connection, pairing information for the mobile device to connect to the medication dispensing cabinet using a different type of connection than the first short range wireless connection;
automatically establishing a second short range wireless connection, of the different type of connection, between the medication dispensing cabinet and a mobile device circuitry based on the pairing information;
providing, from the mobile device to the medication dispensing cabinet via the second short range wireless connection, a request for access to the medication dispensing cabinet; and
receiving an indication that a medication was dispensed from the medication dispensing cabinet based on the request.

13. The method of claim 12, further comprising:
authorizing the user to dispense the medication for a patient, wherein the request is provided when the user is authorized to dispense the medication for the patient and a container storing the medication within the medication dispensing cabinet is unlocked based on the request; and
automatically causing the container to become locked responsive to receiving the indication that the medication was dispensed.

14. The method of claim 12, further comprising:
receiving, from a server, information regarding a medication order associated with the medication;
sending dispense information to the server, the dispense information indicating that the medication was dispensed to the user from the medication dispensing device.

15. The method of claim 12, the method further comprising:
sending a user identification of the user to the medication dispensing cabinet via the first short range wireless connection; and
receiving, from a server, after sending the user identification via the first short range wireless connection, the pairing information for the mobile device to connect to the medication dispensing cabinet,
wherein the second short range wireless connection is established based on the pairing information received from the server.

16. The method of claim 12, the method further comprising:
receiving, at the mobile device from a server, a list of available medication orders for one or more patients associated with the user;
receiving, via a user interface operating on the mobile device, a selection of a patient of the one or more patients or of a medication order corresponding to the medication; and
communicating the selection to the medication dispensing cabinet contemporaneous with the request for access.

17. The method of claim 12, the method further comprising:
establishing the first short range wireless connection between the medication dispensing cabinet and the mobile device using a first communication device implemented by the mobile device;
sending a user identification of the user to the medication dispensing cabinet via the first short range wireless connection;
receiving, by the mobile device from the medication dispensing cabinet, the pairing information via the first short range wireless connection; and
establishing, based on pairing information received via the first short range wireless connection, the second short range wireless connection using a second communication device implemented by the mobile device.

18. A medication dispensing cabinet comprising:
a plurality of lockable containers; and
an access control unit configured to control access to the lockable containers based on commands received from a remote computing device,
the medication dispensing cabinet being configure to:
establish a first short range wireless connection between the medication dispensing cabinet and a first mobile device circuitry associated with a user;
determine, based on information obtained from the first short range wireless connection, pairing information for a second mobile device circuitry to connect to the medication dispensing cabinet using a different type of connection;

automatically establish a second short range wireless connection, different than the first short range wireless connection, between the medication dispensing cabinet and the second mobile device circuitry based on the pairing information; and receive, from the second mobile device circuitry at the medication dispensing cabinet via the second short range wireless connection, a request for access to the medication dispensing cabinet; and cause to be provided, based on the request, access to a medication within the medication dispensing cabinet.

19. The medication dispensing cabinet of claim 18, wherein the medication dispensing cabinet comprises a plurality of lockable containers, the medication dispensing cabinet further configured to:

authorize the user to dispense the medication for a patient; and unlock only a container of the plurality of locking containers that stores the medication based on the request for access and the authorizing.

20. The medication dispensing cabinet of claim 18, further comprising:

providing the pairing information to the first mobile device circuitry via the first short range wireless connection;

receive, after providing the pairing information, a connection request from the second mobile device circuitry to establish the second short range wireless connection; and establish the second short range wireless connection responsive to the connection request, wherein the first mobile device circuitry and second mobile device circuitry are different communication circuitries implemented on a user device.

\* \* \* \* \*